(12) United States Patent
Mantell

(10) Patent No.: US 9,861,377 B2
(45) Date of Patent: *Jan. 9, 2018

(54) UNFOCUSED ELECTROHYDRAULIC LITHOTRIPTER

(71) Applicant: Northgate Technologies, Inc., Elgin, IL (US)

(72) Inventor: Robert Mantell, Arlington Heights, IL (US)

(73) Assignee: NORTHGATE TECHNOLOGIES, INC., Elgin, IL (US)

( * ) Notice: Subject to any disclaimer, the term of this patent is extended or adjusted under 35 U.S.C. 154(b) by 207 days.

This patent is subject to a terminal disclaimer.

(21) Appl. No.: 14/852,051

(22) Filed: Sep. 11, 2015

(65) Prior Publication Data

US 2016/0022295 A1 Jan. 28, 2016

Related U.S. Application Data

(63) Continuation of application No. PCT/IB2014/000275, filed on Mar. 10, 2014.

(60) Provisional application No. 61/775,907, filed on Mar. 11, 2013.

(51) Int. Cl.
*A61B 17/22* (2006.01)

(52) U.S. Cl.
CPC .......... *A61B 17/22022* (2013.01); *A61B 2017/22025* (2013.01); *A61B 2017/22028* (2013.01)

(58) Field of Classification Search
CPC .... A61B 17/22022; A61B 2017/22025; A61B 2017/22028
See application file for complete search history.

(56) References Cited

U.S. PATENT DOCUMENTS

| | | |
|---|---|---|
| 4,191,189 A | 3/1980 | Barkan |
| 4,203,429 A | 5/1980 | Vasilevsky et al. |
| 4,577,255 A | 3/1986 | Martin |
| 4,595,019 A | 6/1986 | Shene et al. |
| 4,927,427 A | 5/1990 | Kriauciunas et al. |
| 5,152,768 A | 10/1992 | Bhatta |
| 5,224,468 A | 7/1993 | Grunewald et al. |
| 5,540,702 A | 7/1996 | Walz |
| 6,319,261 B1 | 11/2001 | Bowers |
| 6,726,681 B2 | 4/2004 | Grasso, III et al. |
| 6,893,450 B2 | 5/2005 | Foster |
| 7,087,061 B2 | 8/2006 | Chernenko et al. |
| 7,104,983 B2 | 9/2006 | Grasso, III et al. |
| 7,189,209 B1 | 3/2007 | Ogden et al. |
| 7,364,554 B2 | 4/2008 | Bolze et al. |
| 7,867,178 B2 | 1/2011 | Simnacher |
| 7,985,189 B1 | 7/2011 | Ogden et al. |
| 7,988,631 B2 | 8/2011 | Bohris |
| 8,088,073 B2 | 1/2012 | Simnacher et al. |
| 8,092,401 B2 | 1/2012 | Schultheiss |
| 2007/0239082 A1 | 10/2007 | Schultheiss et al. |
| 2008/0033323 A1 | 2/2008 | Meirer et al. |
| 2014/0257323 A1 | 9/2014 | Mantell |

*Primary Examiner* — Ashley Fishback
(74) *Attorney, Agent, or Firm* — Brinks Gilson & Lione

(57) ABSTRACT

Electrohydraulic lithotripters comprising a plurality of electrohydraulic probes are disclosed. Each probe of the plurality of probes comprise a first electrode and a second electrode positioned at a distal end of the probe such that when the probe is discharged, an electric arc between the first electrode and the second electrode produces a shockwave that radiates from the distal end of the probe. A first probe and a second probe of the plurality of probes may be configured to discharge simultaneously or sequentially.

30 Claims, 16 Drawing Sheets

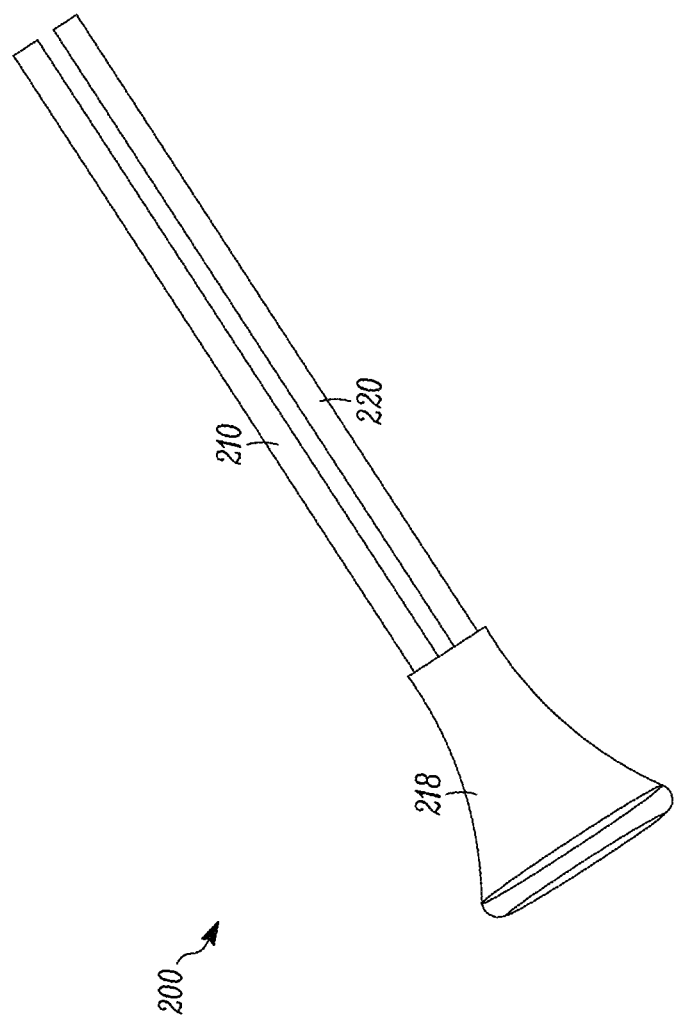

SECTION A-A

UNFOCUSED ELECTROHYDRAULIC LITHOTRIPTER

RELATED APPLICATIONS

This application is a continuation of International Application No. PCT/IB2014/000275, filed on Mar. 10, 2014, pending, which claims the benefit of U.S. Provisional Application No. 61/775,907, filed on Mar. 11, 2013, both of which are incorporated herein by reference.

TECHNICAL FIELD

The present disclosure relates to electrohydraulic lithotripters, and in particular, an unfocused electrohydraulic lithotripter.

BACKGROUND

Electrohydraulic lithotripsy, both intracorporeal ("IEHL") and extracorporeal ("ESWL"), has been used in the medical field, primarily for breaking concretions in the urinary or biliary track. Conventional ESWL lithotripsy produces a focused or reflected shockwave that radiates axially from a distal end of the lithotripsy electrode. This form of treatment has been adapted for generating a shockwave projected to a specific spot within an organism, or at the surface of an organism. Those adaptations utilize various wave shaping methods, usually in the form of elliptical reflection, to project the maximum power to a focal point inside an organism or on the surface of an organism. The focal point receives the largest impact from the shockwave, with degradation in the strength of the shockwave taking the form of an hourglass-type shape on both sides of the focal point, the largest impact occurring at the narrowest part of the hourglass shape.

Techniques for shaping shockwaves produced by electrohydraulic lithotripsy are complex and costly. Significant factors in the focusing and shaping of the shockwave include the shape and positioning of a lithotripsy electrode, as well as the power supplied to the electrodes. For these reasons, known ESWL electrohydraulic lithotripters utilize a single electrode to insure that the impact of the shockwave is maximized at the intended focal point. However, use of a single focused electrode has a number of performance limitations, including for example, the size of generated wave fronts. Known devices are therefore limited by complexity of design, cost, and performance capabilities. Accordingly, improved electrohydraulic lithotripters are desirable.

BRIEF SUMMARY

In one aspect an electrohydraulic lithotripter includes a plurality of electrohydraulic probes. Each probe of the plurality of probes has a first electrode and a second electrode positioned at a distal end of the probe such that when the probe is discharged in a fluid environment, an electric arc between the first electrode and the second electrode produces a shockwave that radiates from the distal end of the probe. A first probe and a second probe of the plurality of probes are configured to discharge simultaneously.

In another aspect, a distal end of the first probe and a distal end of the second probe may be aligned in a plane. Alternatively, a distal end of the first probe may be positioned in a first plane and a distal end of the second probe may be positioned in a second plane, where the first plane is different than the second plane.

In another aspect, the electrohydraulic lithotripter includes a third probe. A central axis of the first probe, a central axis of the second probe, and a central axis of the third probe may not all be positioned in a same plane. The first probe, the second probe, and the third probe may be configured to discharge simultaneously.

In another aspect, an electrohydraulic lithotripter includes a plurality of electrohydraulic probes. Each probe of the plurality of probes has a first electrode and a second electrode positioned at a distal end of the probe such that when the probe is discharged in a fluid environment, an electric arc between the first electrode and the second electrode produces a shockwave that radiates from the distal end of the probe. A first probe and a second probe of the plurality of probes are configured to discharge sequentially.

In another aspect, a distal end of the first probe and a distal end of the second probe may be aligned in a plane. Alternatively, a distal end of the first probe may be positioned in a first plane and a distal end of the second probe may be positioned in a second plane, where the first plane is different than the second plane.

In another aspect, the electrohydraulic lithotripter includes a third probe. A central axis of the first probe, a central axis of the second probe, and a central axis of the third probe may not all be positioned in a same plane. The first probe, the second probe, and the third probe may be configured to discharge sequentially.

In yet another aspect, an electrohydraulic lithotripter includes at least one electrohydraulic probe. Each probe of the at least one probe has a first electrode and a second electrode positioned at a distal end of the probe, such that when the probe is discharged in a fluid environment, an electric arc between the first electrode and the second electrode produces a shockwave that radiates from the distal end of the probe. A flexible encapsulating member at least partially surrounds the distal end of each probe of the at least one probe. A plate positioned relative to the distal end of each probe of the at least one probe receives the shockwave that radiates from the distal end of each probe.

In another aspect, the plate may be positioned within the flexible encapsulating member. Alternatively, the plate may be positioned outside the flexible encapsulating member, in which case, the plate may be coated with a medicament.

In another aspect, the plate may include at least one opening.

In another aspect, the plate may be formed of a rigid material. Alternatively, the plate may be formed of a flexible material.

In another aspect, the at least one probe includes two or more probes.

In yet another aspect, an electrohydraulic lithotripter for extracorporeal administration of electrohydraulic lithotripsy includes at least one electrohydraulic probe. Each probe of the at least one probe has a first electrode and a second electrode positioned at a distal end of the probe, such that when the probe is discharged in a fluid environment, an electric arc between the first electrode and the second electrode produces an unfocused shockwave that radiates from the distal end of the probe.

In another aspect, the electrohydraulic lithotripter may be characterized by the absence of a flexible encapsulating member at least partially surrounding the distal end of each probe of the at least one probe. Alternatively, the electrohydraulic lithotripter may further include a flexible encapsulating member extracorporeally positionable against a tissue, the flexible encapsulating member at least partially surrounding the distal end of each probe of the at least one probe.

In another aspect, the at least one probe comprises a first probe and a second probe. The first probe and the second probe may be configured to discharge simultaneously, or the first probe and the second probe are configured to discharge sequentially.

BRIEF DESCRIPTION OF THE DRAWINGS

FIG. 2A is a perspective view of a second embodiment of an electrohydraulic lithotripter having two electrohydraulic probes;

DETAILED DESCRIPTION

The present disclosure is directed to unfocused electrohydraulic lithotripsy ("EHL") for use both intracorporeally and extracorporeally. Generally, EHL probes include a first electrode and a second electrode positioned at a distal end of the probe. A difference in voltage polarities between the first and second electrodes causes an electric arc, resulting in a shockwave that radiates from the lithotripsy probe. Depending on the shape and positioning of the electrodes, the shockwave may be focused toward a specific region of tissue.

As described herein, unfocused EHL is accomplished by using at least one, and in some cases two or more, EHL probes. The administration of unfocused EHL may be advantageous, for example, in the creation of various shockwave strengths, wave front sizes, wave shapes, or to vary the frequency of shockwaves, as desired, for the treatment of tissues. Such treatments could range, for example, from lightly "massaging" a tissue, to tissue oblation, or cellular disturbance, and potential cellular modification. Areas that may benefit from this treatment could include, for example, tumors, decubitus ulcers, wounds, bone spurs, calcium deposits, arthritic areas, etc.

In one implementation, the EHL probes described below may be delivered to a proper channel of a heart by threading (or pre-loading) the EHL probes through a center lumen of a catheter or balloon device. The catheter may be threaded through appropriate veins or arteries to address concretion either forming in vessels or even in the valves of the heart or other organs. In other implementations, the EHL probes described below may be delivered to a small lumen of a body organ for the purpose of disturbing or disrupting (distressing) tissue of the body organ in such a way as to cause a stricture or a "scarring" of the tissue for the purpose of creating a permanent stricture or blockage of the lumen. In other implementations, the EHL probes described below may be used extracorporeally, for example, by positioning a fluid-filled encapsulating member that encapsulates the EHL probe(s) in contact with the tissue to be treated, or by placing the target tissue (e.g., a bone spur on a foot) and the EHL probe(s) in a fluid-filled basin.

Figure 1A:
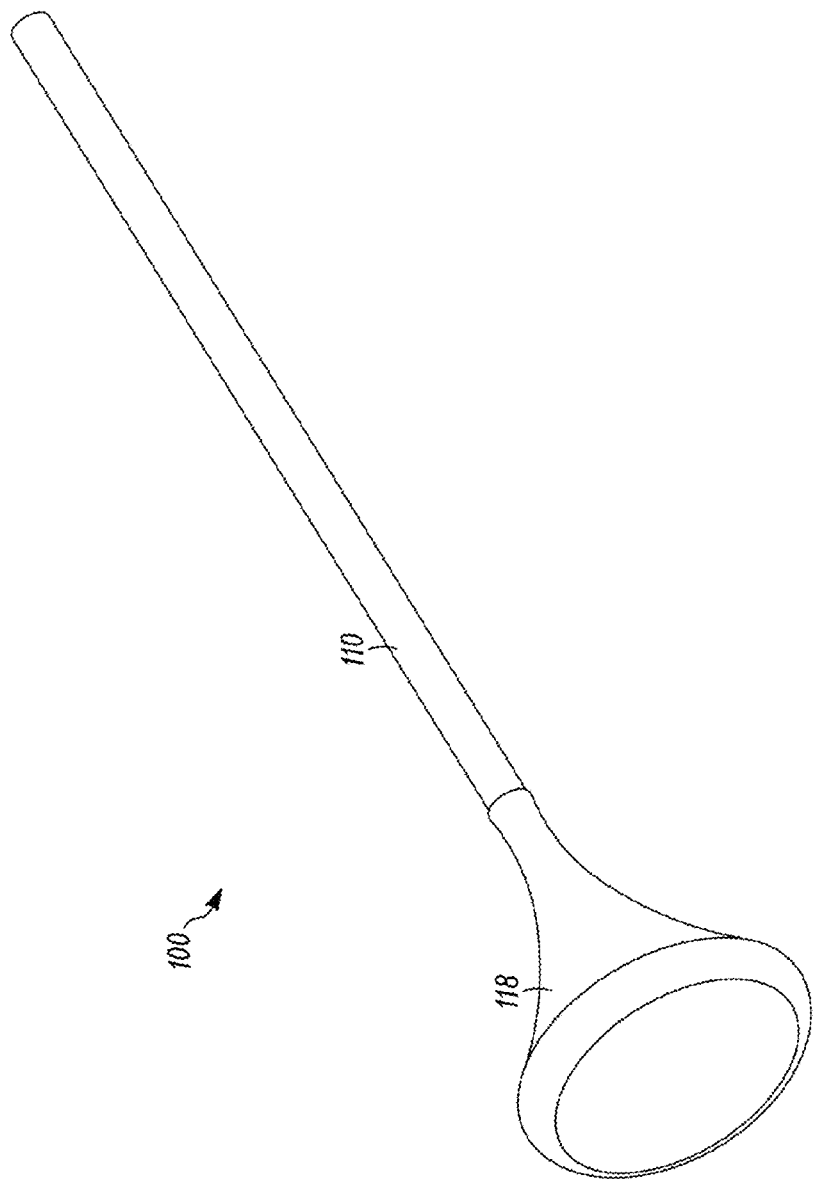
FIG. 1A is a perspective view of an electrohydraulic lithotripter having a single electrohydraulic probe.
Figure 1B:
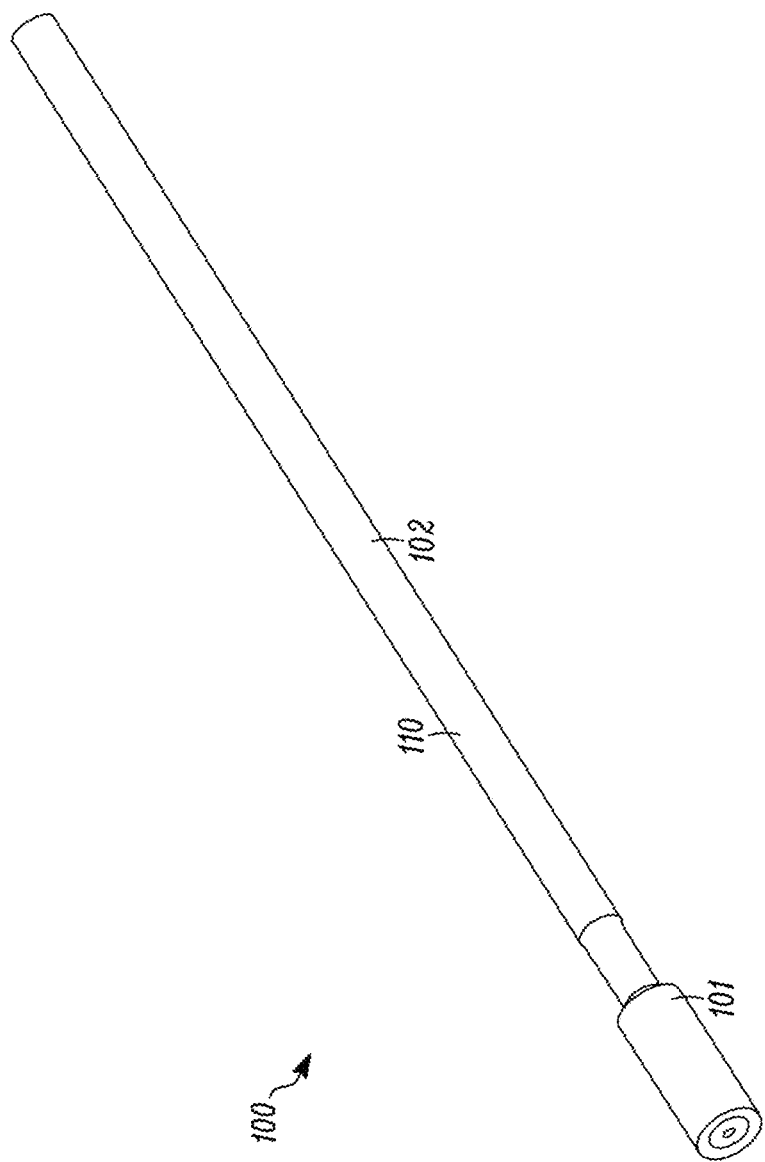
FIG. 1B is a perspective view of the electrohydraulic lithotripsy probe of FIG. 1A, shown without the flexible encapsulating member.
Figure 1C:
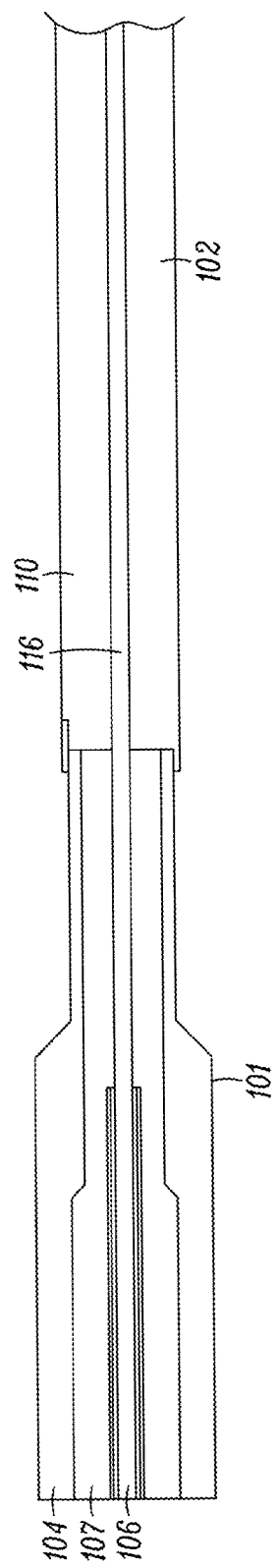
FIG. 1C is a cross-sectional view of the tip of the electrohydraulic lithotripsy probe of FIG. 1B.

Referring to FIGS. 1A-C, a first embodiment of an electrohydraulic lithotripter 100 is shown. The electrohydraulic lithotripter 100 includes an EHL probe 110 having a lithotripsy probe tip 101, an insulating body 102, a first electrode 104, and a second electrode 106. In one implementation, the first electrode 104, the second electrode 106, or both, includes an electrically conductive material such as copper, silver, or stainless steel.

As shown in this embodiment, the first electrode 104 and the second electrode 106 of the EHL probe 110 are cylindrical, with the second electrode 106 concentrically aligned with first electrode 104. An insulating material 107 is disposed in the annular gap formed between the first electrode 104 and the second electrode 106. The distal end of the first electrode 104 is annular, whereas the distal end of the second electrode 106 is circular. However, it is envisioned that other EHL probes having electrodes of different shapes and orientations may also be used without departing from the concepts described herein. For example, changing the probe dimensions, particularly the annular gap between the first electrode 104 and the second electrode 106, can alter the strength and the size of the shockwave (e.g., the larger the annular gap, the greater the strength and the size of the shockwave). Alternatively, a probe may include an electrode comprised of an array of conductive elements.

The first electrode 104 is electrically coupled with a first electrically conductive structure (not shown) in the EHL probe 110. As known in the art, the first electrically conductive structure may be coupled with an electrical source, such as an electrohydraulic generator (Autolith, Supplied by Northgate Technologies Inc.), used to charge the first electrode 104 to a first polarity. The second electrode 106 is electrically coupled with a second electrically conductive structure 116 in the EHL probe 110. As known in the art, the second electrically conductive structure 116 may be coupled with an electrical source and used to charge the second electrode 106 to a second polarity, which is opposite to the first polarity of the first electrode 104.

In one implementation, the first electrode 104 is an anode and the second electrode 106 is a cathode, wherein in other implementations, the first electrode 104 is a cathode and the second electrode 106 is an anode. In implementations having more than one probe, it is envisioned that a single anode may be used with multiple cathodes, or conversely, a single cathode may be used with multiple anodes. When the first electrode 104 is charged to a first polarity via the first conductive structure and the second electrode 106 is charged to a second, opposite polarity via the second conductive structure 116, a discharge of electricity occurs between the first electrode 104 and the second electrode 106 (an electric arc) when the potential between the first electrode 104 and the second electrode 106 reaches the breakdown voltage for the media separating the electrodes.

As shown in this embodiment, at least a portion of the EHL probe tip 101 including the first electrode 104 and the second electrode 106 is surrounded by a flexible encapsulating member 118, such as a balloon, comprising a watertight flexible material, such as Mylar. The flexible encapsulating member 118 encapsulates a liquid, such as saline. However, other liquids can be used. In general, the less ionic content of the fluid, the greater the breakdown voltage, and the stronger the shockwave, whereas the greater the ionic content, the less the breakdown voltage, and the weaker the shockwave.

When an electrical arc occurs between the first electrode 104 and the second electrode 106 as described above, the electrical arc causes a steam bubble in the liquid of the flexible encapsulating member 118. The steam bubble rapidly expands and contracts back on itself. As the steam bubble contracts, a pressure wave (a shockwave) is created in the liquid of the flexible encapsulating member 118 that radiates away from the EHL probe tip 101. In other implementations, a flexible encapsulating member 118 does not surround the EHL probe tip 101, for example, when the EHL probe 100 is used intracorporeally within a fluid-filled body cavity, or when the EHL probe 100 is used extracorporeally, such as in a fluid-filled basin.

Figure 2B:
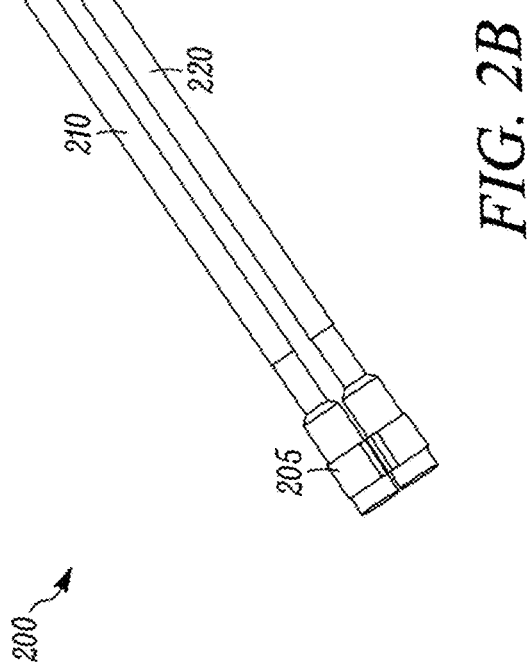
FIG. 2B is a perspective view of the electrohydraulic lithotripsy probes of FIG. 2A, shown without the flexible encapsulating member.

Referring to FIGS. 2A-B, a second embodiment of an electrohydraulic lithotripter 200 is shown. The electrohydraulic lithotripter 200 includes a first EHL probe 210 and a second EHL probe 220. The first EHL probe 210 and the second EHL probe 220 may be constructed and operate in the same manner as describe above with regards to the EHL probe 110, although it is envisioned that other EHL probes having electrodes of different shapes and orientations may also be used without departing from the concepts described herein. The first EHL probe 210 and the second EHL probe 220 may be connected together by a band 205.

As shown in this embodiment, the distal ends of the first EHL probe 210 and the second EHL probe 220 are aligned, i.e., they lie in the same plane. In other implementations, the distal ends lie in different planes. As also shown in this embodiment, a flexible encapsulating member 218 surrounds a distal end of the electrohydraulic lithotripter 200. In other implementations, a flexible encapsulating member 218 does not surround a distal end of the electrohydraulic lithotripter 200.

Figure 3A:
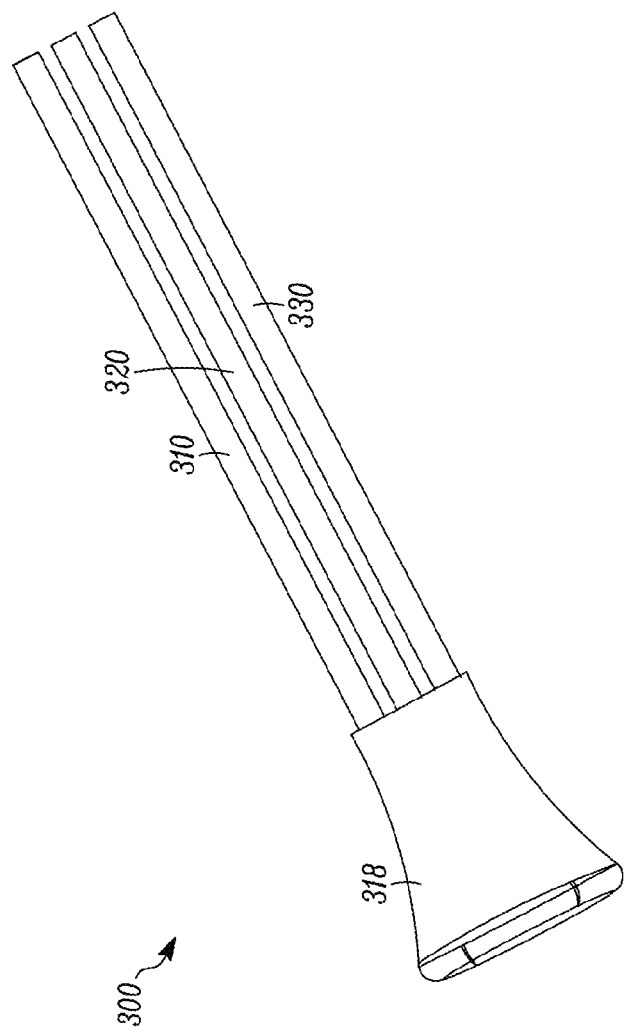
FIG. 3A is a perspective view of a third embodiment of an electrohydraulic lithotripter having three electrohydraulic probes.
Figure 3B:
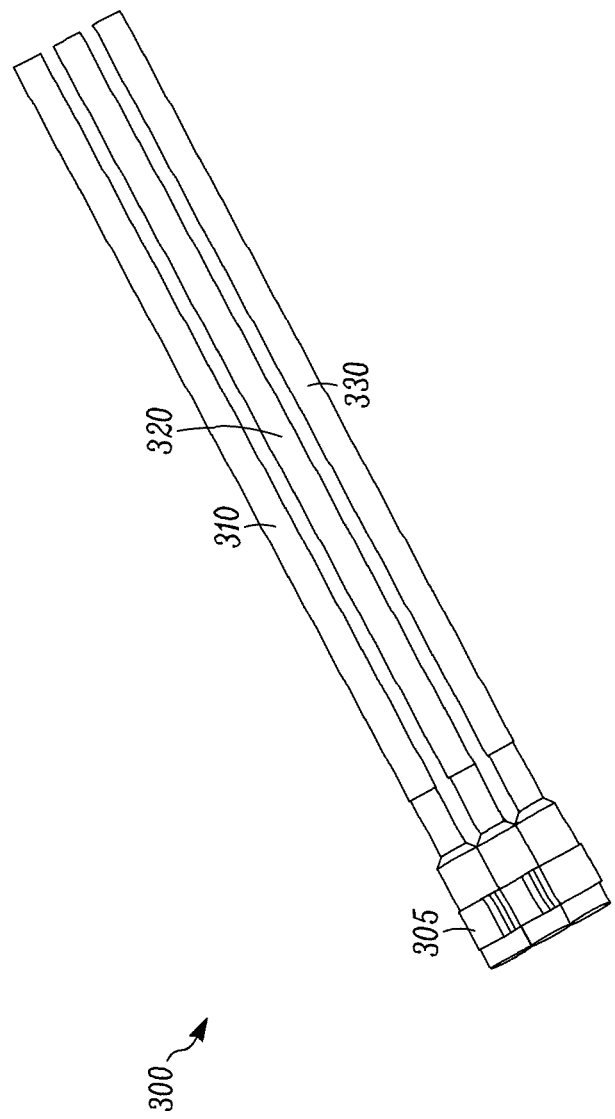
FIG. 3B is a perspective view of the electrohydraulic lithotripsy probes of FIG. 3A, shown without the flexible encapsulating member.

Referring to FIGS. 3A-B, a third embodiment of an electrohydraulic lithotripter 300 is shown. The electrohydraulic lithotripter 300 includes a first EHL probe 310, a second EHL probe 320, and a third EHL probe 330. The first EHL probe 310, the second EHL probe 320, and the third EHL probe 330 may be constructed and operate in the same manner as describe above with regards to the EHL probe 110, although it is envisioned that other EHL probes having electrodes of different shapes and orientations may also be used without departing from the concepts described herein. The first EHL probe 310, the second EHL probe 320, and the third EHL probe 330 may be connected together by a band 305.

As shown in this embodiment, the distal ends of the first EHL probe 310, the second EHL probe 320, and the third EHL probe 330 are aligned, i.e., they lie in the same plane. In other implementations, the distal ends lie in different planes. Also as shown in this embodiment, the first EHL probe 310, the second EHL probe 320, and the third EHL probe 330 are arranged such that their axes lie in the same plane. In other implementations, their axis are offset, for example, in a triangular configuration. Furthermore, as shown in this embodiment, a flexible encapsulating member 318 surrounds a distal end of the electrohydraulic lithotripter 300. In other implementations, a flexible encapsulating member 318 does not surround a distal end of the electrohydraulic lithotripter 300.

Figure 4A:
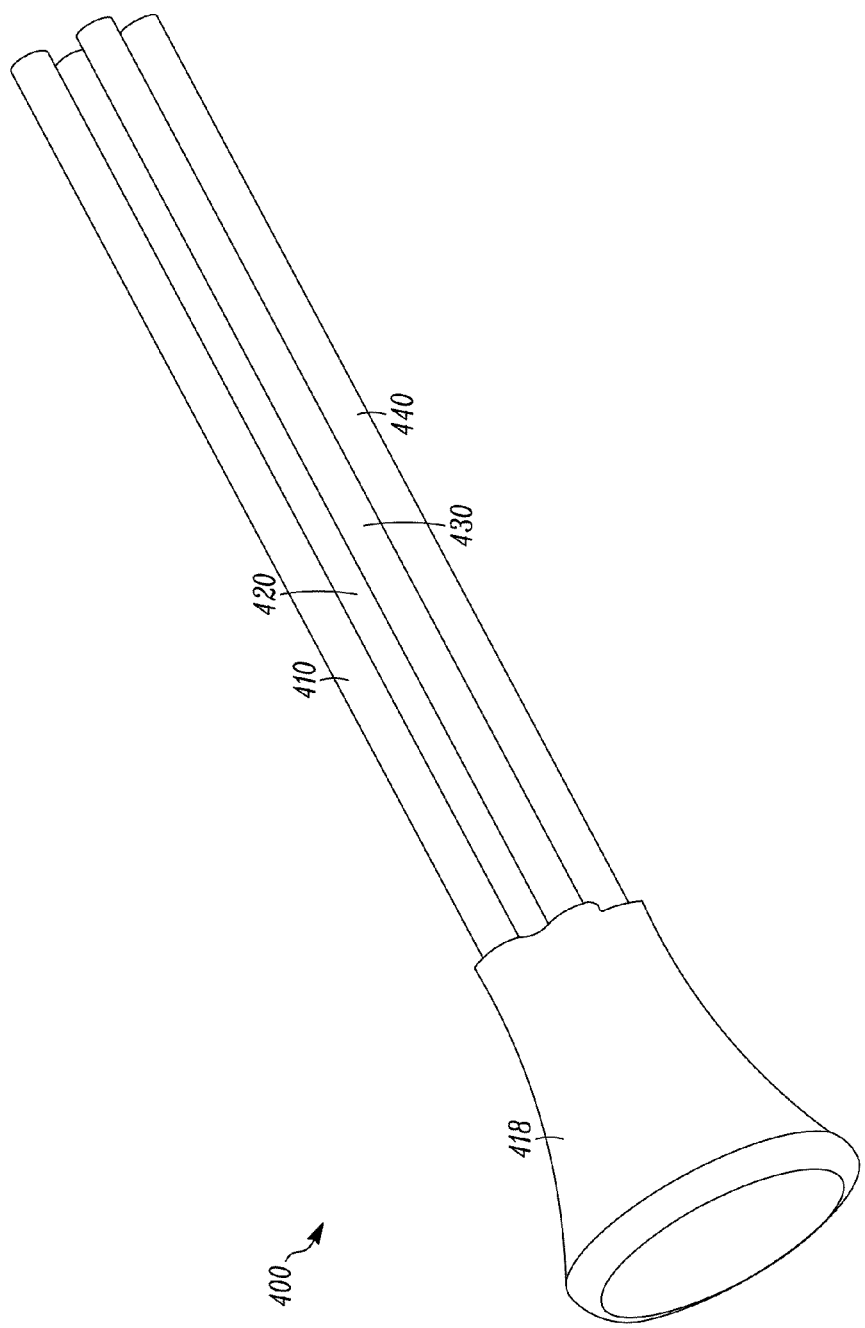
FIG. 4A is a perspective view of a fourth embodiment of an electrohydraulic lithotripter having four electrohydraulic probes.
Figure 4B:
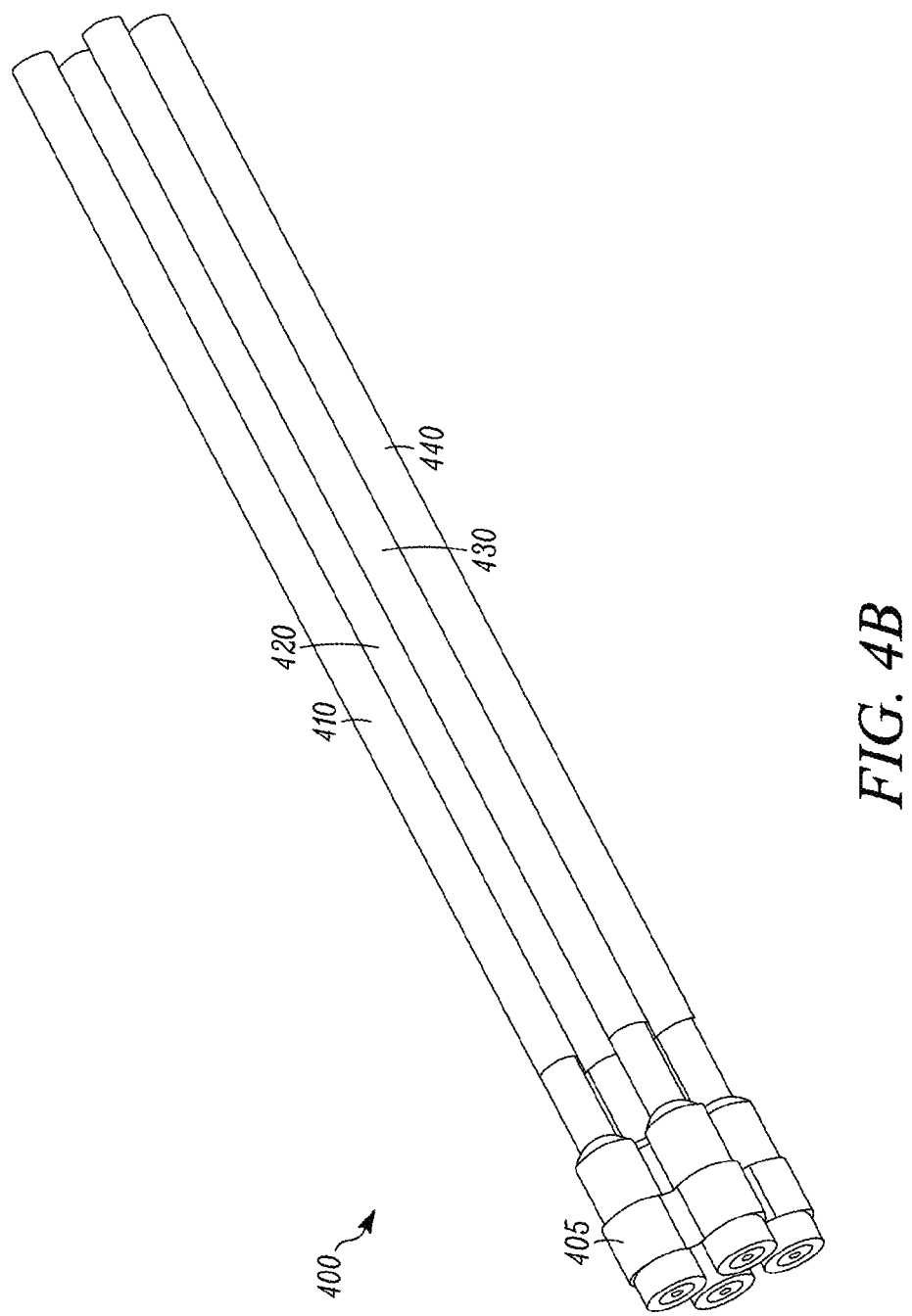
FIG. 4B is a perspective view of the electrohydraulic lithotripsy probes of FIG. 4A, shown without the flexible encapsulating member.

Referring to FIGS. 4A-B, a fourth embodiment of an electrohydraulic lithotripter 400 is shown. The electrohydraulic lithotripter 400 includes a first EHL probe 410, a second EHL probe 420, a third EHL probe 430, and a fourth EHL probe 440. The first EHL probe 410, the second EHL probe 420, the third EHL probe 430, and the fourth EHL probe 440 may be constructed and operate in the same manner as describe above with regards to the EHL probe 110, although it is envisioned that other EHL probes having electrodes of different shapes and orientations may also be used without departing from the concepts described herein. The first EHL probe 410, the second EHL probe 420, the third EHL probe 430, and the fourth EHL probe 440 may be connected together by a band 405.

As shown in this embodiment, the distal ends of the first EHL probe 410, the second EHL probe 420, the third EHL probe 430, and the fourth EHL probe 440 are aligned, i.e., they lie in the same plane. In other implementations, the distal ends lie in different planes. Also as shown in this embodiment, the first EHL probe 410 and the fourth EHL probe 440 are arranged such that their axes lie in the same plane, while the second EHL probe 420 and the third EHL probe 430 are arranged such that their axes lie in the same plane. In other implementations, all axes may lie in the same plane, or they may be arranged, for example, in a square configuration. Furthermore, as shown in this embodiment, a flexible encapsulating member 418 surrounds a distal end of the electrohydraulic lithotripter 400. In other implementations, a flexible encapsulating member 418 does not surround a distal end of the electrohydraulic lithotripter 400.

Figure 5A:
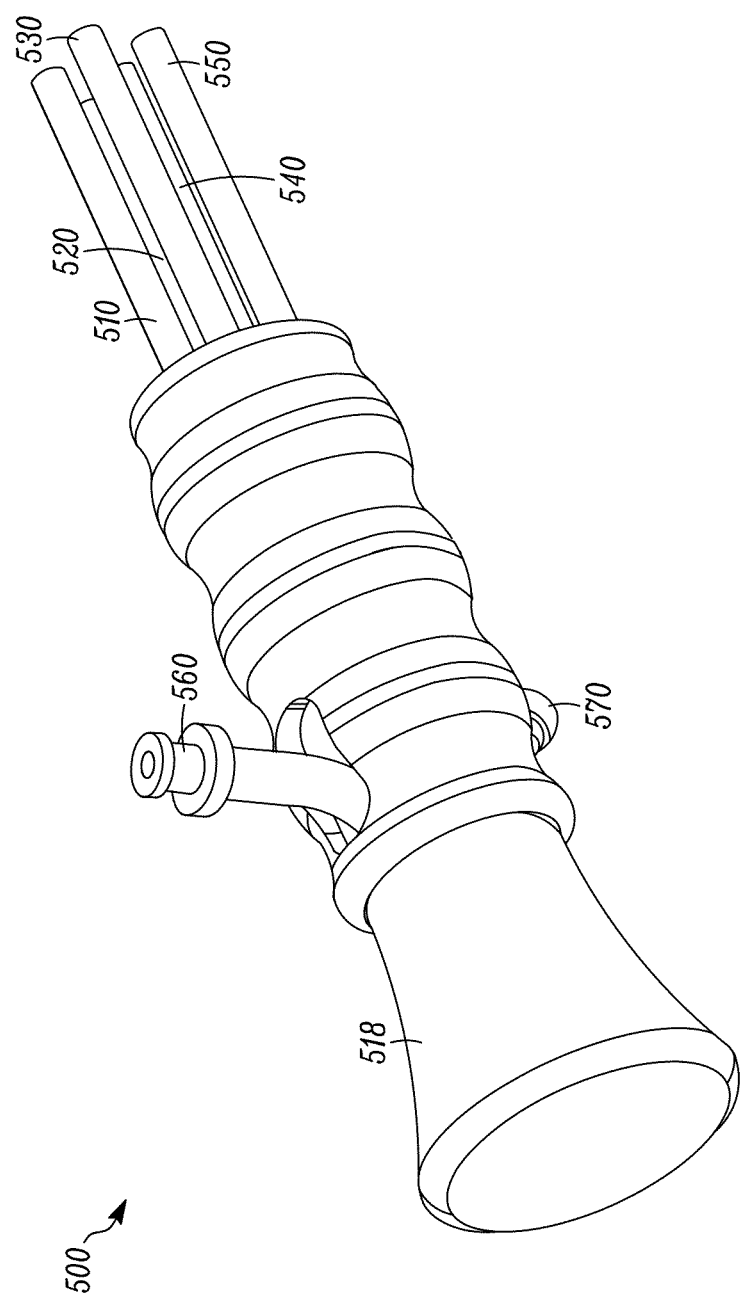
FIG. 5A is a perspective view of a fifth embodiment of an electrohydraulic lithotripter having five electrohydraulic probes.
Figure 5B:
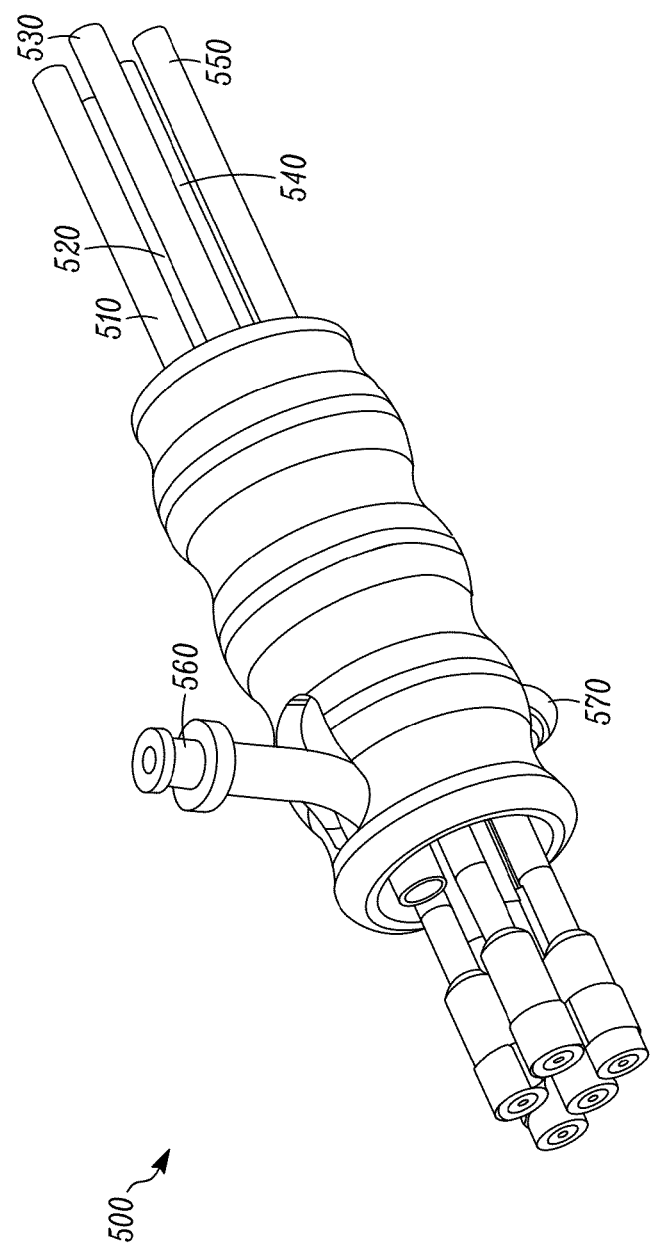
FIG. 5B is a perspective view of the electrohydraulic lithotripsy probes of FIG. 5A, shown without the flexible encapsulating member.
Figure 5C:
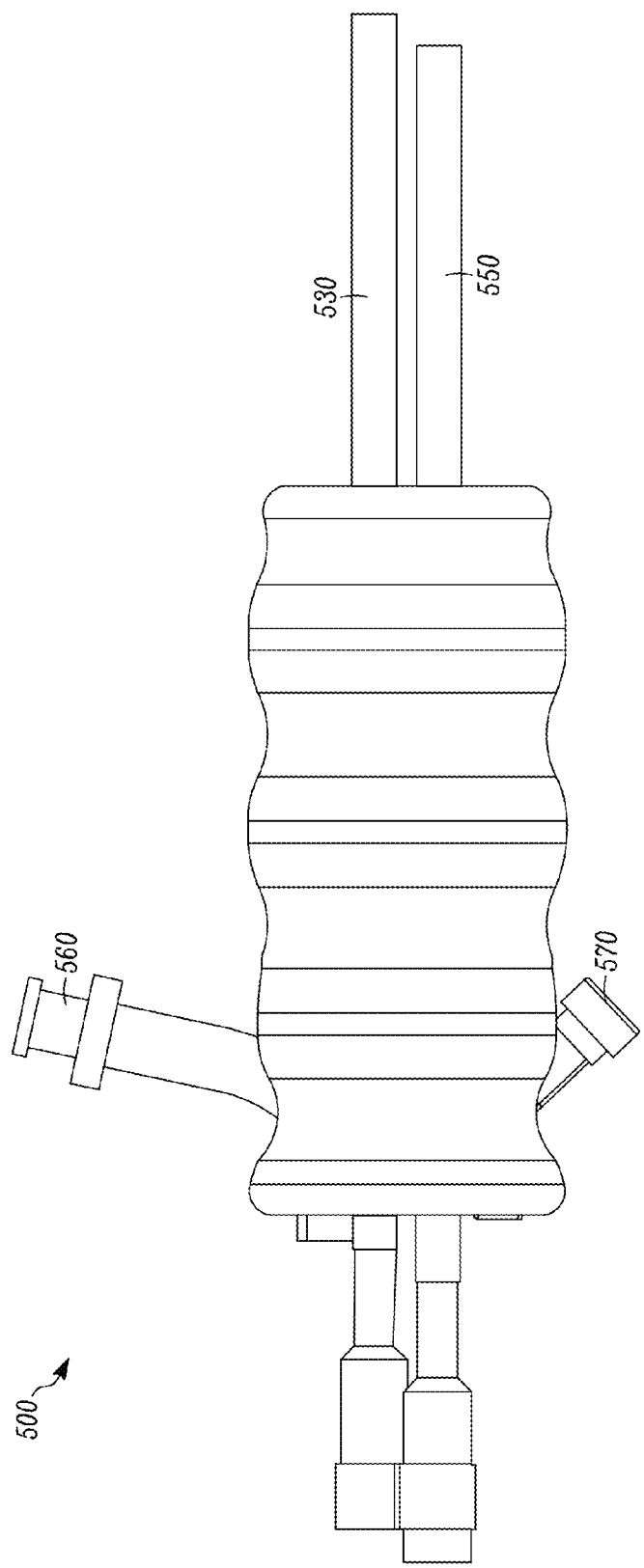
FIG. 5C is a side view of the electrohydraulic lithotripsy probes of FIG. 5B.

Referring to FIGS. 5A-B, a fifth embodiment of an electrohydraulic lithotripter 500 is shown. The electrohydraulic lithotripter 500 includes a first EHL probe 510, a second EHL probe 520, a third EHL probe 530, a fourth EHL probe 540, and a fifth EHL probe 550. The first EHL probe 510, the second EHL probe 520, the third EHL probe 530, the fourth EHL probe 540, and the fifth EHL probe 550 may be constructed and operate in the same manner as describe above with regards to the EHL probe 110, although it is envisioned that other EHL probes having electrodes of different shapes and orientations may also be used without departing from the concepts described herein. The first EHL probe 510, the second EHL probe 520, the third EHL probe 530, the fourth EHL probe 540, and the fifth EHL probe 550 may be connected together by a band 505.

As shown in this embodiment, the distal ends of the first EHL probe 510 and the third EHL probe 530, are aligned, i.e., they lie in the same plane, whereas the distal ends of the second EHL probe 520, the fourth EHL probe 540, and the fifth EHL probe 550 are aligned. In other implementations, the distal ends of all probes lie in the same plane. Also as shown in this embodiment, the first EHL probe 510 and the third EHL probe 530 are arranged such that their axes lie in the same plane, whereas the second EHL probe 520, the fourth EHL probe 540, and the fifth EHL probe 550 are arranged such that their axes lie in the same plane. In other implementations, all axes may lie in the same plane, or they may be arranged, for example, in a circular configuration. Furthermore, as shown in this embodiment, a flexible encapsulating member 518 surrounds a distal end of the electrohydraulic lithotripter 500. In other implementations, a flexible encapsulating member 518 does not surround a distal end of the electrohydraulic lithotripter 500.

As also shown in this embodiment, the electrohydraulic lithotripter 500 may include a first channel (or lumen) 560 and a second channel (or lumen) 570 that are each in communication with an interior of the flexible encapsulating member 518. Although only shown in this embodiment, it should be appreciated that a first channel (or lumen) and a second channel (or lumen) in communication with an interior of a flexible encapsulating member may be included in any of the embodiments described herein. During operation, the first channel 520 may be utilized to infuse a liquid, such as saline, into an interior of the flexible encapsulating member 518 for the purpose of expanding the flexible encapsulating member 518 and providing a medium for creating electrohydraulic effect.

Additionally, the second channel 570 may be utilized to remove the liquid from the interior of the flexible encapsulating member 518 and collapse the flexible encapsulating member 518. In some implementations, the second channel 570 may further be utilized to degass the fluid within the flexible encapsulating member 518 after an electrohydraulic discharge between electrodes.

The circulation of fluid through the interior of the flexible encapsulating member 518 using the first and second channels 560, 570 may be done through manual means such as a syringe, mechanical means such as a pump, or any other means known in the art.

In some implementations, the first and/or second channels 560, 570 may include one or more valves, membranes, or cartridges to assist in injecting a fluid into the interior region of the flexible encapsulating member 518, removing a fluid from the interior region of the flexible encapsulating member 518, or degassing the fluid within the interior region of the flexible encapsulating member 518.

For example, a valve or membrane positioned in or adjacent to the first channel 560 may allow a fluid to flow into the interior region of the flexible encapsulating member 518 while preventing the fluid from entering the first channel 560 from the interior region of the flexible encapsulating member 518. Similarly, a valve or membrane positioned in or adjacent to the second channel 570 may allow a fluid to flow out of the interior region of the flexible encapsulating member 518 while preventing fluid from exiting the second channel 570 and flowing into the interior of the flexible encapsulating member 518. Further, a membrane or cartridge may be positioned in or adjacent to the second channel 570 to assist in degassing fluid within the interior region of the flexible encapsulating member 518. Examples of valves that may be utilized include one-way valves produced by Qosina Corp or Value Plastics. Examples of membranes, such as semipermeable membranes, that may be utilized include those produced by W.L. Gore & Associates, Inc.

Each of the previously described embodiments may be used to provide unfocused EHL. The activation of individual EHL probes creates unfocused shockwaves radiating from each probe. By positioning the probes in a cluster or a particular pattern, an almost infinite number of shockwave patterns may be generated. Such patterns can be used, for example, to create larger wave fronts than a single probe, stronger shockwaves, and different wave shapes. In addition, the probes may be fired or discharged simultaneously, or in sequences, or at various frequencies. Furthermore, the arrangement of probes may be such that distal ends of the probes are staggered, or arranged in different planes, thereby creating additional wave shapes or patterns.

A generator may be set to fire or discharge a particular EHL probe at varying power and at varying frequencies. One suitable generator is the Autolith, supplied by Northgate Technologies, Inc. Other suitable generators are shown and described in U.S. Provisional Patent Application No. 61/684,353, the entirety of which is herein incorporated by reference. The device could use different capacitors and switching techniques to change the output of a particular EHL probe, or probes. Redundant circuitry could be also be used if necessary to discharge a large number of probes simultaneously, or in specific sequences, or in patterns, depending on the desired treatment.

Figure 6A:
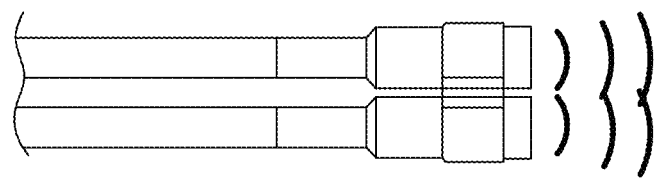
FIGS. 6A-D are illustrations of the wave shapes and patterns achievable by the disclosed embodiments.
Figure 6B:
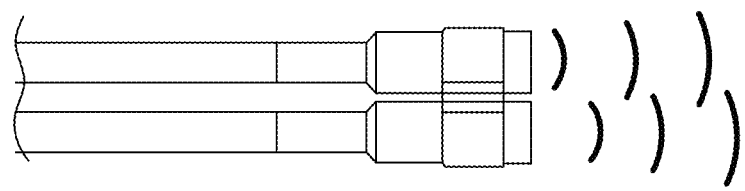
Figure 6C:
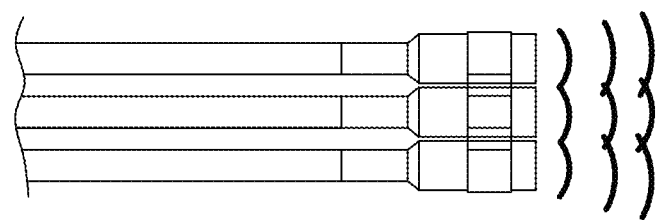
Figure 6D:
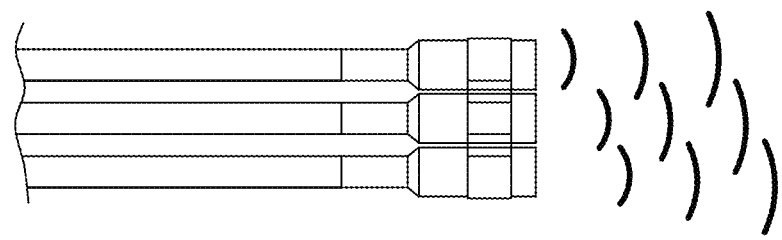

By way of example, FIGS. 6A-6D illustrate some of the wave shapes and patterns achievable by the previously described embodiments. As shown in FIG. 6A, the EHL probes of the electrohydraulic lithotripter 200 may be fired or discharged simultaneously, thereby producing a wave front having an increased sized. Alternatively, as shown in FIG. 6B, the probes of the electrohydraulic lithotripter 200 may be fired or discharged sequentially to create an alternating waveform. Similarly, as shown in FIG. 6C, the EHL probes of the electrohydraulic lithotripter 300 may be fired or discharged simultaneously, thereby producing a wave front having an even larger size. Likewise, as shown in FIG. 6D, the EHL probes of the electrohydraulic lithotripter 300 may be fired or discharged sequentially, thereby creating a cascading waveform. It will be appreciated that additional wave shapes and patterns may be achieved by applying the same firing or discharge concepts to the other embodiments described herein.

Furthermore, additional wave strengths, shapes, and patterns may be generated by altering the shapes and orientations of electrodes within individual EHL probes of a particular embodiment of an electrohydraulic lithotripter, for example, by changing the probe dimensions, such as the annular gap between the first electrode and the second electrode.

In embodiments having a flexible encapsulating member, the strength of the shockwave(s) delivered to a tissue may be selectively adjusted by changing the volume of fluid in the flexible encapsulating member. Because the strength of a shockwave delivered to a tissue is dependent on the distance from the distal end of the EHL probe(s) to the tissue, the strength of a shockwave may be increased or decreased by increasing or decreasing the volume of the fluid in the flexible encapsulating member. These embodiments may also include means for measuring the distance between the distal ends of individual EHL probe(s) and the flexible encapsulating member.

In other embodiments, the strength of the shockwave(s) delivered to a tissue may be selectively adjusted by axially repositioning particular EHL probes within the electrohydraulic lithotripter. For example, the electrohydraulic lithotripter 400 includes a first EHL probe 410, a second EHL probe 420, a third EHL probe 430, and a fourth EHL probe 440. The EHL probes are connected together by a band 405. As shown in FIG. 4B, the distal ends of the first EHL probe 410, the second EHL probe 420, the third EHL probe 430, and the fourth EHL probe 440 are aligned, i.e., they lie in the same plane. However, a user may axially advance, for example, the first EHL probe 410 and the fourth EHL probe 440, relative to the band 405, the second EHL probe 420, and the third EHL probe 430, such that the distal ends of the first EHL probe 410 and the fourth EHL probe 440 lie in a different plane than the distal ends of the second EHL probe 420 and the third EHL probe 430. These embodiments may also include means for locking the positions of the EHL probes relative to one another.

In other embodiments, the shockwave(s) may be discharged toward a conductive surface, such as a pad or a plate, for purposes of transferring the shockwave to particular tissues areas. For example, a plate may be used to distribute or spread the shockwave over the surface of the plate. Alternatively, a plate having a number of openings may be used to focus the discharged shockwave(s) through the openings to treat a targeted tissue area. Such a plate may be made of either flexible or rigid materials, depending on the desired shockwave deflection, absorption, or transfer characteristics, and can be positioned either inside or outside of the flexible encapsulating member. If positioned on the outside of the flexible encapsulating member, the plate may be coated or infused with a medication to assist in the tissue treatment.

Figure 7A:
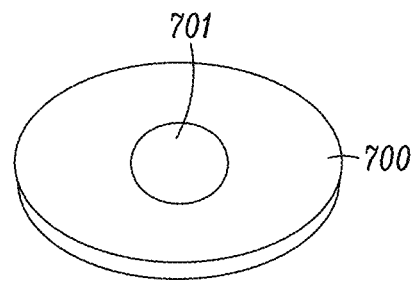
FIGS. 7A-C are exemplary illustrations of a plate useable with any of the embodiments described herein.
Figure 7B:
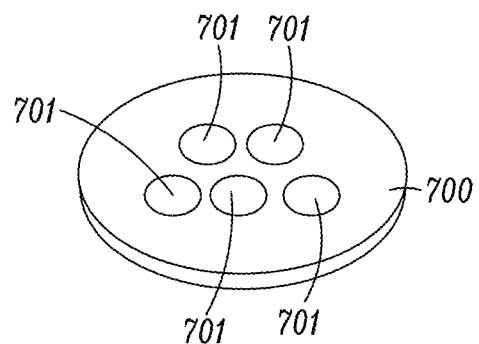
Figure 7C:
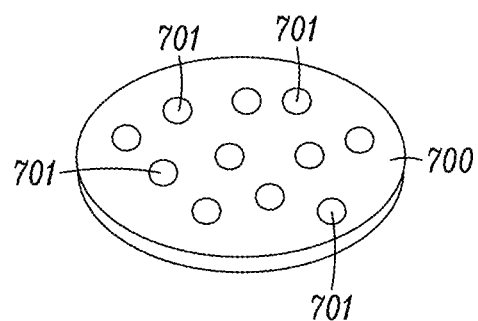
Figure 8D:
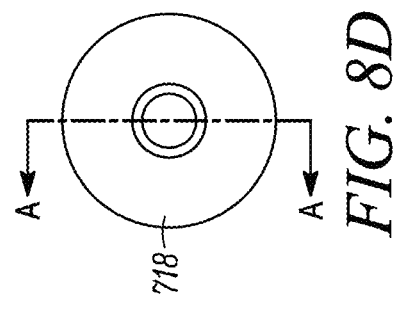
FIGS. 8A-E are various perspective and side views of an alternatively shaped lithotripsy probe tip.
Figure 8C:
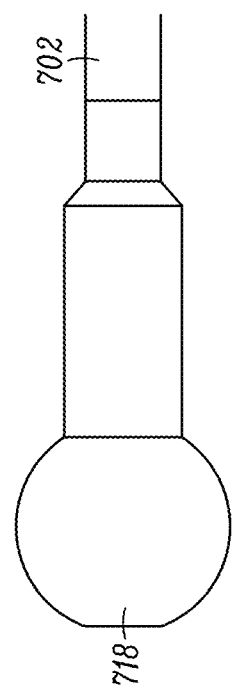
Figure 8E:
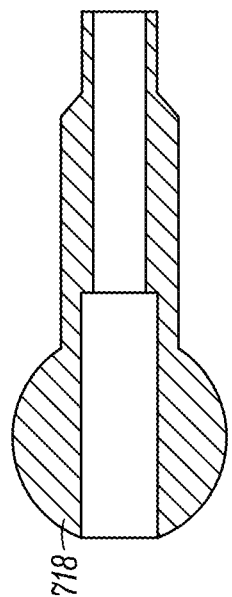
Figure 8A:
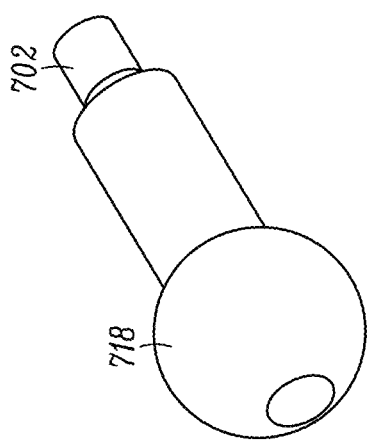
Figure 8B:
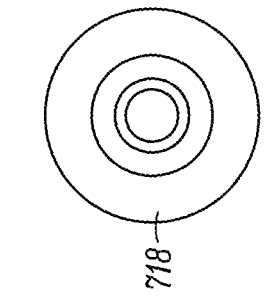

FIGS. 7A-7C are exemplary illustrations of a plate 700 useable with any of the embodiments described herein. As shown in FIG. 7A, the plate 700 may have a single, centrally positioned opening 701 intended to allow the shockwave(s) discharged from the EHL probe(s) to pass therethrough. Or, as shown in FIG. 7B, the plate 700 may include a plurality of openings 701, aligned with the EHL probes of the associated electrohydraulic lithotripter, for example, the five EHL probes of the electrohydraulic lithotripter 500. As shown, in FIG. 7C, the plate 700 may include a plurality of openings in an arrangement, for example, intended to diffuse the shockwave(s) discharged from the EHL probe(s). Alternatively, the plate may not have any openings.

The recent introduction of endoscopes that are designed to reach more remote locations in the body has presented various difficulties in trying to reach these areas of the body. In order to fragment and destroy concretions at remote locations within the body, endoscopes and other instruments, such as electrohydraulic lithotripsy probes, may have to maneuver through extremely tortuous paths to conduct diagnostic and operating procedures. For example, bends as sharp as 90 degrees, and in some instances, as much as 120 degrees or more, must be traversed to reach the desired location. Because of frictional forces in the lumens of scopes or catheters, or tubes, and the creases or "wrinkles" that develop in the inner walls of these lumens, it is often very difficult to push delicate devices such as guide-wires, forceps, baskets, lasers, or electrohydraulic lithotripsy probes through the lumens to reach the desired site.

In the case of lasers and electrohydraulic lithotripsy probes, it is extremely difficult or impossible, partially because of the lack of stiffness in the laser fiber or lithotripsy probe. Furthermore, the tip of these devices is usually shaped as a square, or includes beveled edges, which have been insufficient to prevent lodging, kinking, or resistance caused from too much friction, to progress past or through the tortuous angles, thereby rendering it impossible in some cases for the laser fibers or electrohydraulic lithotripsy probes to reach the target area. Some approaches to obviate these problems have included increasing the size and stiffness of the fiber or probe, covering the probe with more lubricious materials (e.g., Teflon), applying a hydrophilic coating to the probe, and sever beveling of the fiber or probe tip. While these techniques have led to improvement, they have not solved the problem sufficiently.

Turning to FIGS. 8A-E, various perspective and side views of an alternatively shaped lithotripsy probe tip 718 are shown. Like the previously described lithotripsy probe tips, the lithotripsy probe tip 718 is disposed on the end of an insulating body 702 of an electrohydraulic lithotripter. The lithotripsy probe tip 718 may be utilized in place of any of the previously described lithotripsy probe tips, as well as in other electrohydraulic lithotripters.

The lithotripsy probe tip 718 is adapted to improve the delivery of an electrohydraulic lithotripter to a remote location in the body. As shown, the lithotripsy probe tip 718 is spherically shaped. Significantly, the distal surface of the lithotripsy probe tip 718 essentially presents a "round surface" to the structural areas it may contact. All of the previous improvements (e.g., stiffer shafts, slippery sheaths, hydrophilic coatings, etc.) could be included and used in conjunction with the improved tip shape. As shown, there would be an opening in the tip, close to tangent or tangent to the rounded surface, so that no edges would be presented to the lumen surfaces that would catch on the interior lumen bends or "wrinkles." It should be appreciated that the shape of the tip does not have to be perfectly round, but that the surfaces presented to the lumen walls would have to have the circular radii necessary to approximate a round or circular surface.

In a preferred embodiment, the diameter of the spherically shaped lithotripsy probe tip 718 is approximately 1.5 mm (0.585 inches) or less, as that is approximately the largest lumen diameter currently in use in endoscopes used in urology or gastrointestinal applications. The diameter could be as small as 0.5 mm for some applications. The tip size, however, could be larger or smaller depending on the available lumen, endoscope, or body area being accessed. Ultimately, the size of the tip would be governed by the lumen size through which it is threaded.

Figure 9:
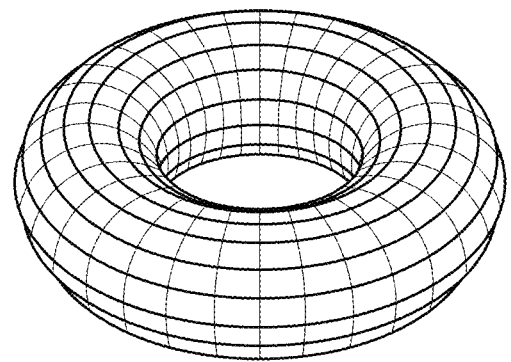
FIG. 9 is an illustration of another alternatively shaped lithotripsy probe tip; and, FIG. 10 is an illustration of another alternatively shaped lithotripsy probe tip.
Figure 10:
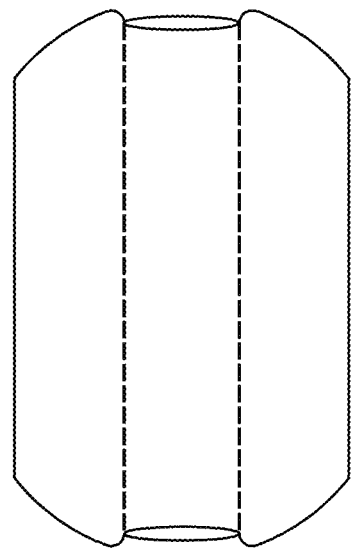

In alternative embodiments, the shape of the tip could be any other rounded shape, including, for example, a "donut" shape, as shown in FIG. 9. The "donut" shaped tip could, for example, have a radius of about 0.018 inches, a diameter of 0.036 inches, an axial length of 0.025 inches, and an inner lumen diameter of 0.008 inches. Alternatively, the shape of the tip could be a bead shape having a spherical head with flat or cylindrical sides, as shown in FIG. 10. The bead shaped tip could, for example, have a radius of about 0.026 inches in the spherical head, a diameter of 0.05 inches in the cylindrical sides, an axial length of 0.052 inches, and an inner lumen diameter of 0.028 inches. General tolerances for these dimensions above could range between +/−0.003 to 0.005 inches. It should be appreciated that so long as the lead surfaces of the tip present a "round" surface for contacting the lumen, just about any shape may be used.

The various lithotripsy probe tips described above may be constructed of many types of materials, preferably metal, plastic, or glass. Depending on the material used, the tip may be integral to the function of the device (such as glass in a laser fiber, or metal in a lithotripsy probe tip), or could be added on to and/or bonded on an existing tip design.

It is intended that the foregoing detailed description e regarded as illustrative rather than limiting, and that it be understood that it is the following claims, including all equivalents, that are intended to define the spirit and scope of this invention.

What is claimed is:

1. An electrohydraulic lithotripter comprising:
a plurality of electrohydraulic probes, each probe of the plurality of probes comprising a first electrode and a second electrode positioned at a distal end of the probe such that when the probe is discharged in a fluid environment, an electric arc between the first electrode and the second electrode produces a shockwave that radiates from the distal end of the probe; and,
one or more rounded lead contact surfaces positioned at a distal end of each probe of the plurality of probes, the one or more rounded lead contacts surfaces adapted to receive a force opposing advancement of the electrohydraulic lithotripter through a lumen;
wherein a first probe and a second probe of the plurality of probes are configured to discharge simultaneously; and,
wherein a position of a distal end of the first probe relative to a position of a distal end of the second probe is selectively adjustable.

2. The electrohydraulic lithotripter of claim 1, wherein the position of the distal end of the first probe is selectively adjustable for positioning in a plane that is substantially parallel to the distal end of the first probe and the distal end of the second probe.

3. The electrohydraulic lithotripter of claim 1, wherein the position of the distal end of the first probe is selectively adjustable for positioning in a first plane that is substantially parallel to the distal end of the first probe, with the distal end of the second probe being positioned in a second plane that is substantially parallel to the distal end of the second probe, the first plane being different than the second plane.

4. The electrohydraulic lithotripter of claim 1, wherein each probe of the plurality of probes are connected together by a band.

5. The electrohydraulic lithotripter of claim 1, wherein the one or more rounded lead contacts surfaces comprises a spherical shape.

6. The electrohydraulic lithotripter of claim 1, wherein the one or more rounded lead contacts surfaces comprises a donut shape.

7. The electrohydraulic lithotripter of claim 1, wherein the one or more rounded lead contacts surfaces comprises a bead shape characterized by a rounded lead contact surface and a cylindrical side surface.

8. An electrohydraulic lithotripter comprising:
a plurality of electrohydraulic probes, each probe of the plurality of probes comprising a first electrode and a second electrode positioned at a distal end of the probe such that when the probe is discharged in a fluid environment, an electric arc between the first electrode and the second electrode produces a shockwave that radiates from the distal end of the probe;
one or more rounded lead contact surfaces positioned at a distal end of each probe of the plurality of probes, the one or more rounded lead contacts surfaces adapted to receive a force opposing advancement of the electrohydraulic lithotripter through a lumen;
wherein a first probe and a second probe of the plurality of probes are configured to discharge sequentially; and,
wherein a position of a distal end of the first probe relative to a position of a distal end of the second probe is selectively adjustable.

9. The electrohydraulic lithotripter of claim 8, wherein the position of the distal end of the first probe is selectively adjustable for positioning in a plane that is substantially parallel to the distal end of the first prove and the distal end of the second probe.

10. The electrohydraulic lithotripter of claim 8, wherein the position of the distal end of the first probe is selectively adjustable for positioning in a first plane that is substantially parallel to the distal end of the first probe, with the distal end of the second probe being positioned in a second plane that is substantially parallel to the distal end of the second probe, the first plane being different than the second plane.

11. The electrohydraulic lithotripter of claim 8, wherein each probe of the plurality of probes are connected together by a band.

12. The electrohydraulic lithotripter of claim 8, wherein the one or more rounded lead contacts surfaces comprises a spherical shape.

13. The electrohydraulic lithotripter of claim 8, wherein the one or more rounded lead contacts surfaces comprises a donut shape.

14. The electrohydraulic lithotripter of claim 8, wherein the one or more rounded lead contacts surfaces comprises a bead shape characterized by a rounded lead contact surface and a cylindrical side surface.

15. An electrohydraulic lithotripter comprising:
a plurality of electrohydraulic probes, each probe of the plurality of probes having a first electrode and a second electrode positioned at a distal end of the probe, such that when the probe is discharged in a fluid environment, an electric arc between the first electrode and the second electrode produces a shockwave that radiates from the distal end of the probe;
a flexible encapsulating member at least partially surrounding the distal end of each probe of the plurality of probes; and,
a plate positioned relative to the distal end of each probe of the plurality of probes for receiving the shockwave that radiates from the distal ends of each probe;
wherein the plate comprises a surface area sized to receive the shockwave that radiates from the distal end of each probe of the plurality of probes; and,
wherein the plate is positioned entirely within the flexible encapsulating member.

16. The electrohydraulic lithotripter of claim 15, wherein the plate comprises at least one opening.

17. The electrohydraulic lithotripter of claim 15, wherein the plate is formed of a rigid material.

18. The electrohydraulic lithotripter of claim 15, wherein the plate is formed of a flexible material.

19. An electrohydraulic lithotripter for extracorporeal administration of electrohydraulic lithotripsy comprising:
a plurality of electrohydraulic probes, each probe of the plurality of probes comprising a first electrode and a second electrode positioned at a distal end of the probe, such that when the probe is discharged in a fluid environment, an electric arc between the first electrode and the second electrode produces an unfocused shockwave that radiates from the distal end of the probe;
wherein a position of a distal end of a first probe of the plurality of probes relative to a position of a distal end of a second probe of the plurality of probes is selectively adjustable.

20. The electrohydraulic lithotripter of claim 19, characterized by the absence of a flexible encapsulating member at least partially surrounding the distal end of each probe of the plurality of probes.

21. The electrohydraulic lithotripter of claim 19, further comprising a flexible encapsulating member extracorporeally positionable against a tissue, the flexible encapsulating member at least partially surrounding the distal end of each probe of the plurality of probes.

22. The electrohydraulic lithotripter of claim 19, wherein the first probe and the second probe are configured to discharge simultaneously.

23. The electrohydraulic lithotripter of claim 19, wherein the first probe and the second probe are configured to discharge sequentially.

24. The electrohydraulic lithotripter of claim 19, wherein the position of the distal end of the first probe is selectively adjustable for positioning in a plane that is substantially parallel to the distal end of the first probe and the distal end of the second probe.

25. The electrohydraulic lithotripter of claim 19, wherein the position of the distal end of the first probe is selectively adjustable for positioning in a first plane that is substantially parallel to the distal end of the first probe, with the distal end of the second probe being positioned in a second plane that is substantially parallel to the distal end of the second probe, the first plane being different than the second plane.

26. An electrohydraulic lithotripter comprising:
  a plurality of electrohydraulic probes, each probe of the plurality of probes having a first electrode and a second electrode positioned at a distal end of the probe, such that when the probe is discharged in a fluid environment, an electric arc between the first electrode and the second electrode produces a shockwave that radiates from the distal end of the probe;
  a flexible encapsulating member at least partially surrounding the distal end of each probe of the plurality of probes; and,
  a plate positioned relative to the distal end of each probe of the plurality of probes for receiving the shockwave that radiates from the distal ends of each probe;
  wherein the plate comprises a surface area sized to receive the shockwave that radiates from the distal end of each probe of the plurality of probes; and,
  wherein the plate is positioned entirely outside the flexible encapsulating member.

27. The electrohydraulic lithotripter of claim 26, wherein the plate is formed of a rigid material.

28. The electrohydraulic lithotripter of claim 26, wherein the plate is formed of a flexible material.

29. The electrohydraulic lithotripter of claim 26, wherein the plate comprises a plurality of openings.

30. The electrohydraulic lithotripter of claim 29, wherein each opening of the plurality of openings is aligned with a probe of the plurality of probes.

* * * * *